United States Patent [19]

Voges et al.

[11] Patent Number: 5,162,538
[45] Date of Patent: Nov. 10, 1992

[54] ANTIVIRAL NEW PEPTIDES

[75] Inventors: Klaus-Peter Voges; Dieter Häbich; Jutta Hansen, all of Wuppertal; Arnold Paessens, Haan; Christoph Meichsner, Hofheim, all of Fed. Rep. of Germany

[73] Assignee: Bayer Aktiengesellschaft, Leverkusen, Fed. Rep. of Germany

[21] Appl. No.: 624,173

[22] Filed: Dec. 7, 1990

[30] Foreign Application Priority Data

Dec. 14, 1989 [DE] Fed. Rep. of Germany ....... 3941235

[51] Int. Cl.$^5$ .......................................... C07D 213/56
[52] U.S. Cl. ..................................... 546/336; 546/337
[58] Field of Search ................. 514/357; 546/336, 337

[56] References Cited

FOREIGN PATENT DOCUMENTS 0337714 10/1989 European Pat. Off. ............ 546/337
0357332 3/1990 European Pat. Off. .
8803436 6/1989 PCT Int'l Appl. .
2203740 4/1987 United Kingdom ................ 546/337

OTHER PUBLICATIONS

Mitsuya et al., Retroviruses in Human Lymphoma/Leukemia, pp. 277-288, 1985.
Sardstrom et al., Drugs, vol. 34, pp. 373-390, 1987.
Methods in Enzymology, vol. XXXIV, "Affinity Techniques, Enzyme Purification: Part B", Bovine Trypsin and Thrombin, Hixson, Jr. and A. H. Nishikawa, pp. 440-448, Academic Press, 1974.
Methods in Enzymology, vol. XXXIV, "Affinity Techniques, Enzyme Purification: Part B", Chymotrypsin(s), Tomlinson et al., pp. 415-420, Academic Press 1974.
Affinity Chromatography, Biospecific Sorption; Affinity Chromatography of Chymotrypsin on Soybean Trypsin Inhibitor Sepharose: Applications In Genetics and Nuclide Labelling, Gabel, Kasche, Amneus and Lundqvist, pp. 99-102, Pergamon Press, 1977.
Applied Microbiology and Biotechnology, Springer-Verlag 1979, Biotechnol. 6.; p. 195 (1979).
"Recovery of Free Enzymes from Product Liquors by Bio-Affinity Adsorption: Trypsin Binding by Immobilised Soybean Inhibitor", Halling and Dunnill, The Journal of Biological Chemistry, vol. 255, No. 15, Aug. 10, 1980, p. 7089.
"Human Red Cell Purine Nucleoside Phosphorylase, Purification By Biospecific Affinity Chromatography and Physical Properties", Osborne, Mar. 17, 1980.
Hoppe-Seyler's Z. Physiol. Chem., vol. 361, p. 543, Apr. 1980, "Purification of Human and Bovine Alkaline Phosphatases by Affinity Chromatography", Mossner, Boll and Pfleiderer.
Analytical Biochemistry, vol. 107, p. 341 (1980), "Affinity Chromatographic Sorting of Carboxypeptidase A and its Chemically Modified Derivatives", Cueni, Bazzone, Riordan & Vallee, Mar. 31, 1980.
Hoppe-Seyler's Z. Physiol. Chem., vol. 359, p. 1019, Aug. 1978, "Affinity Chromatography of Bovine Bran β-Hexosaminidases with Substrate as Affinity Ligand", Lisman and Overdijk, May 1978.
Biochem. J. (1978), vol. 175, p. 125, "Purification of the Hexokinases by Affinity Chromatography on Sepharose-N-Aminoacylglucosamine Derivatives", Wright, Warsy, Holroyde and Trayer, Feb. 1978.
Archives of Biochemistry and Biophysics, vol. 198, No. 2, Dec. 1979, p. 533, "Quantitative Affinity Chromatography of α-Chymotrypsin", Dunn and Gilbert, Aug. 10, 1979.
Understanding Enzymes, Third Ed. (Horwood Press, 1991), pp. 309-310, Trevor Palmer.
Science, vol. 247, pp. 454-456, "A Synthetic HIV-1 Protease Inhibitor with Antiviral Activity Arrests HIV-Like Particle Maturation".
J. Hansen et al., (1988), EMBO Journal, vol. 7, No. 6, pp. 1785-1791.
Journal of Virological Methods, 20 (1988), pp. 309-321.

Primary Examiner—C. Warren Ivy
Assistant Examiner—Ba K. Trinh
Attorney, Agent, or Firm—Sprung Horn Kramer & Woods

[57] ABSTRACT

Antiviral new peptides of the formula

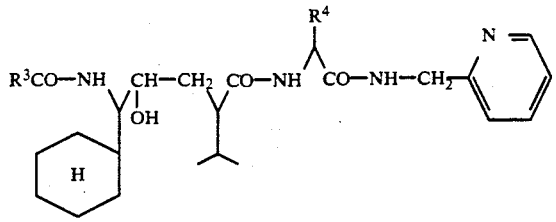

in which
$R^3$ denotes straight-chain or branched alkyl having up to 8 carbon atoms or
denotes aryl having 6 to 10 carbon atoms or tolyl, and
$R^4$ denotes straight-chain or branched alkyl having up to 8 carbon atoms,
and physiologically acceptable salts thereof.

11 Claims, No Drawings

ANTIVIRAL NEW PEPTIDES

The invention relates to new peptides, processes for the preparation thereof and the use thereof as medicaments, in particular as antiviral agents in human and veterinary medicine.

Peptides which have antiviral activity against the human immunodeficiency virus (HIV) are described in GB 2,203,740 and EP-A-2 0,337,714.

The present invention now provides peptides of the general formula (I)

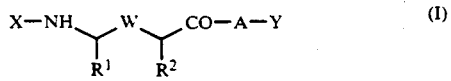

in which
X represents a group of the formula $R^3CO—$, wherein
  $R^3$ denotes straight-chain or branched alkyl having up to 8 carbon atoms or
  denotes aryl having 6 to 10 carbon atoms or tolyl
$R^1$ represents cyclohexylmethyl,
$R^2$ represents isopropyl,
W represents a radical of the formula

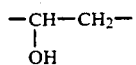

A represents a radical of the formula

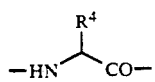

wherein
$R^4$ denotes straight-chain or branched alkyl having up to 8 carbon atoms,
in the D- or L-form or as a mixture of D,L-isomers, preferably in the L-form,
Y represents a group of the formula $—NHR^5$, wherein $R^5$ denotes the group

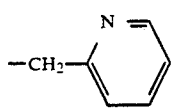

and the physiologically acceptable salts thereof.
The general formula Ia

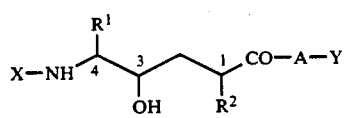

has 3 asymmetric carbon atoms (1, 3 and 4) which, independently of one another, can be present in the R- or S-configuration. Preferably, this group is present in the 1R, 3S, 4S-configuration, 1R, 3R, 4S-configuration, 1S, 3R, 4S-configuration or in the 1S, 3R, 4S-configuration. The 1S, 3S, 4S-configuration is particularly preferred.

Compounds of the general formula (I) according to the invention may be present in the form of the salts thereof. These may be salts with inorganic or organic acids or bases. Preferred acid addition products are salts with hydrochloric acid, hydrobromic acid, hydriodic acid, sulphuric acid, phosphoric acid, or with carboxylic acids such as acetic acid, propionic acid, oxalic acid, glycolic acid, succinic acid, maleic acid, hydroxymaleic acid, methylmaleic acid, fumaric acid, adipic acid, malic acid, tartaric acid, citric acid, benzoic acid, cinnamic acid, lactic acid, ascorbic acid, salicylic acid, 2-acetoxybenzoic acid, nicotinic acid, isonicotinic acid, or sulphonic acids such as methanesulphonic acid, ethanesulphonic acid, benzenesulphonic acid, toluenesulphonic acid, naphthalene-2-sulphonic acid or naphthalenedisulphonic acid.

Preferred compounds of the general formula (I) are those in which
X represents a group of the formula $R^3CO—$, wherein
  $R^3$ denotes straight-chain or branched alkyl having up to 6 carbon atoms, phenyl or tolyl,
$R^1$ represents cyclohexylmethyl,
$R^2$ represents isopropyl,
W represents a radical of the formula

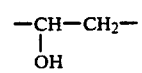

A represents a radical of the formula

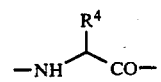

wherein
$R^4$ denotes straight-chain or branched alkyl having up to 6 carbon atoms,
in the D- or L-form, or as a mixture of D,L-isomers, preferably in the L-form,
Y represents a group of the formula $—NHR^5$, wherein $R^5$ denotes the group

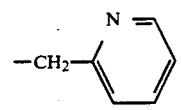

and the physiologically acceptable salts thereof.
Particularly preferred compounds of the general formula (I) are those in which
X represents a group of the formula $R^3CO—$, wherein
  $R^3$ denotes straight-chain or branched alkyl having up to 4 carbon atoms, tolyl or phenyl,
$R^1$ represents cyclohexylmethyl,
$R^2$ represents isopropyl,
W represents a radical of the formula

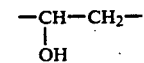

A represents a radical of the formula

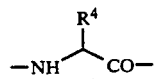

wherein $R^4$ denotes straight-chain or branched alkyl having up to 4 carbon atoms, in the D- or L-form, or as a mixture of D,L-isomers, preferably in the L-form, Y represents a group of the formula $-NHR^5$, wherein $R^5$ denotes the group

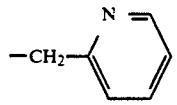

and the physiologically acceptable salts thereof.

Additionally, a process for the preparation of the compounds of the general formula (I) has been found, which process is characterized by the acylation of compounds of the general formula (II)

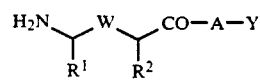 (II)

in which $R^1$, $R^2$, W, A, and Y have the meanings stated above, in inert solvents by a customary method, if appropriate in the presence of a base.

The process according to the invention can be illustrated by the following equation by way of example:

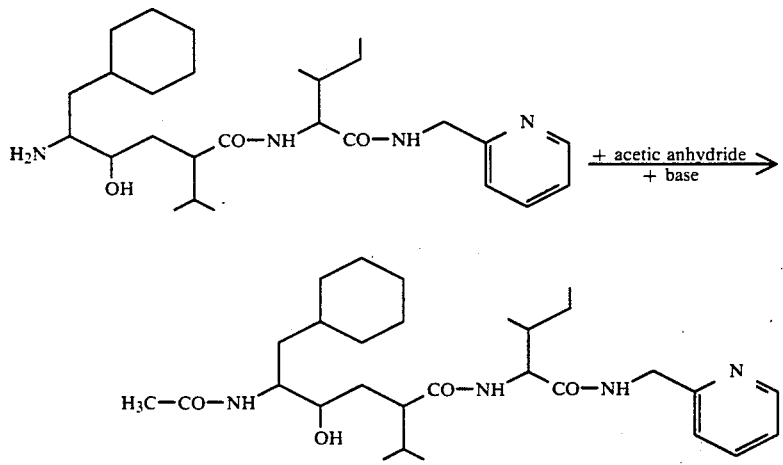

Suitable solvents for the acylation are the customary inert solvents which do not change under the reaction conditions. These preferably include organic solvents such as ethers, for example diethyl ether, glycol monomethyl ether or glycol dimethyl ether, dioxane or tetrahydrofuran, or hydrocarbons such as benzene, toluene, xylene, cyclohexane or petroleum fractions or halogenated hydrocarbons such as dichloromethane, chloroform, carbon tetrachloride, or dimethyl sulphoxide, dimethylformamide, hexamethylphosphoric triamide, ethyl acetate, pyridine, triethylamine or picoline. It is also possible to use mixtures of the stated solvents. Dimethylformamide is particularly preferred.

Suitable acylation agents are for example carboxylic anhydrides, carboxylic acid chlorides or carboxylic acid esters. Carboxylic anhydrides such as, for example, acetic anhydride are preferred.

Suitable bases are the customary organic bases. These preferably include organic amines such as triethylamine, picoline or N-methylpiperidine. N-methylpiperidine is particularly preferred.

The acylation is generally carried out in a temperature range from 0° C. to +80° C., preferably at room temperature.

In this process, the base is employed in an amount of 1.0 to 1000, preferably of 1.0 to 2.0 mols, relative to 1 mol of the compound of the general formula (II).

The compounds of the general formula (II) are known per se or can be prepared by methods customary in peptide chemistry starting from the appropriate carboxylic acid esters ($H_2N-CHR^1-W-CHR^2-COOH$) by reaction with the amino acid residue ($HO-A-Y$) wherein $R^1$, $R^2$, W, A and Y have the meanings stated above).

The compounds of the general formula (I) have extraordinarily strong action against retroviruses. This was proven by experiments using the HIV-specific protease enzyme test.

The result of the example below was obtained using the HIV-test system described in the following reference [cf. Hansen, J., Billich, S., Schulze, T., Sukrow, S. and Mölling, K. (1988), EMBO Journal, Vol. 7, No. 6, pp. 1785–1791]: purified HIV protease was incubated with synthetic peptide which imitates a cleavage site in the Gag-precursor protein and represents an in vivo cleavage site of HIV protease. The resulting cleavage products of the synthetic peptide were analyzed by reverse-phase high performance liquid chromatography (RP-HPLC). The $IC_{50}$ value relates to the substance concentration which causes 50% inhibition of protease activity under the abovementioned test conditions.

| Example No. | $IC_{50}$ (RP-HPLC) |
|---|---|
| 1 | $5 \times 10^{-10}$ M |

Additionally and surprisingly, the compounds according to the invention show an effect in infected cell culture. This was shown by way of example for the Visna virus.

The Visna virus and the HIV virus both belong to the retrovirus subfamily of lentiviruses. Both viruses exhibit a similar genome organization and a complex transcription pattern compared to the other retroviruses. Known inhibitors of HIV also inhibit Visna virus in vitro using comparable concentrations; i.e. this model is suitable for testing and finding HIV inhibitors.

In cell cultures which are infected with Visna virus, pronounced, virus-induced, cytopathic effects appear 5 to 10 days after infection. By treating the infected cell cultures with compounds according to the invention, it was possible to prevent the appearance of these cytopathic effects.

The Visna virus test was carried out according to the method of O. Narayan et al., Journal of Infectious Diseases 135, 5, 1977, 800–806. For this, a compound according to the invention was diluted to non-cytotoxic concentrations in the culture medium in 96-well microtiter plates. Sheep fibroblast cells ($5 \times 10^4$ cells per well) in production medium were then added to each well. Each well then received 15 μl of a Visna virus solution having a titer of approx. $2.5 \times 10^4$ TCID$_{50}$ (TCID=tissue culture infections dose). This virus dose corresponds to a MOI (multiplicity of infection) of approx. 0.05.

Under these infection conditions, a virus-induced, cytopathic effect resulted between day 5 and day 10 in an infection control without substance. The infected and treated cells and the control cells were incubated for 7 days at 37° C. and 5% $CO_2$.

On appearance of the virus-induced, cytopathogenic effect in the untreated virus control the cultures were fixed with formalin and then stained with a Giemsa solution. The inhibitory concentration (IC$_{50}$) was microscopically determined as the concentration at which the cytopathic effect was inhibited by 50% in comparison to the untreated virus control which exhibited 100% cell destruction.

It was found that, for example, the compound from Example I protected the cells infected with Visna virus from the virus-induced cell destruction.

Thus the compounds according to the invention represent valuable active compounds in human and veterinary medicine for the treatment and prophylaxis of diseases caused by retroviruses.

Indication areas which may be mentioned in human medicine are, for example:
1. The treatment or prophylaxis of human retroviral infections.
2. The treatment or prophylaxis of diseases (AIDS) caused by HIV I (human immunodeficiency virus; formerly named HTLV III/LAV) and HIV II, and the stages associated therewith such as ARC (AIDS related complex) and LAS (lymphadenopathy syndrome) and also the hyperimmunity and encephalopathy caused by these viruses.
3. The treatment or the prophylaxis of an HTLV I or HTLV II infection.
4. The treatment or the prophylaxis of the AIDS carrier condition.

Indications in veterinary medicine which may be mentioned are, for example:
Infections with
a) Maedivisna (in sheep and goats)
b) progressive pneumonia virus (PPV) (in sheep and goats)
c) caprine arthritis encephalitis virus (in sheep and goats)
d) Zwoegerziekte virus (in sheep)
e) infectious anaemia virus (of the horse)
f) infections caused by feline leukaemia virus
g) infections caused by feline immunodeficiency virus.

The abovementioned points 2, 3 and 4 from the indication area in human medicine are preferred.

The present invention includes pharmaceutical preparations which contain one or more compounds of the formula (I) in addition to non-toxic, inert, pharmaceutically acceptable excipients, or consists of one or more active compounds of the formula (I) and also processes for the production of these preparations.

The active compounds of the formula (I) should generally be present in the pharmaceutical preparations in a concentration of about 0.1 to 99.5, preferably of about 0.5 to 95, % by weight of the total mixture.

The abovementioned pharmaceutical preparations may also contain further pharmaceutical active compounds in addition to the compounds of the formula (I).

The preparation of the abovementioned pharmaceutical preparations takes place in a customary manner by known methods, for example by mixing the active compound(s) with the excipient(s).

In general, it has proved advantageous both in human and veterinary medicine to administer the active compound(s) of the formula (I) in total amounts of about 0.5 to about 500, preferably 5 to 100, mg/kg of body weight every 24 hours, if appropriate in the form of several individual doses, to obtain the desired results. An individual dose preferably contains the active compound(s) in amounts of about 1 to about 80, in particular 1 to 30, mg/kg of body weight. However, it may be necessary to deviate from the dosages mentioned, depending upon the species and body weight of the subject to be treated, the nature and the severity of the disease, the type of preparation and the administration of the medicament and also the period or interval within which the administration takes place.

Appendix to the experimental part

List of the thin layer systems
Ia) $CH_2Cl_2/CH_3OH = 90:1$
Ib) $CH_2Cl_2/CH_3OH = 85:15$

STARTING COMPOUND

EXAMPLE 1

$N_\alpha$-{1-[5-S-amino-6-cyclohexyl-4(S)-hydroxy-2-(1-methyl)ethylhexanoyl]}-S-isoleucinyl-2-pyridylmethylamide

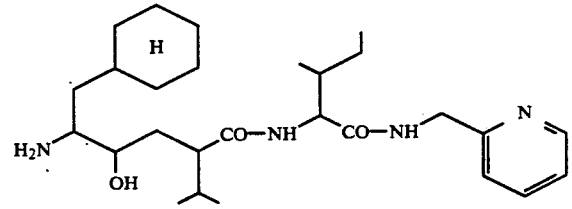

7 g (10.8 mmol) of 3-benzyloxycarbonyl-4(S)-cyclohexylmethyl-2,2-dimethyl-5(S)-{1'-{3'-[2'-(1-methyl)ethyl]propanoyl}-S-isoleucinyl-2-pyridylmethylamide}oxazolidine are dissolved in 120 ml of methanol and 10 ml of glacial acetic acid, and 200 mg of palladium-on-active charcoal are added. A current of $H_2$ is passed through the mixture for 10 h, and the solution is then filtered by suction on kieselguhr and 50 ml of potassium hydrogen sulphate solution are added. After distilling off the methanol the residue is diluted with 80 ml of water and extracted twice with ethyl acetate. The aqueous solution is adjusted to pH 10 using 2N NaOH and extracted three times with ethyl acetate. 3.2 g of a wax-like solid are obtained after drying and concentrating the organic phase.

TLC: $R_f$(Ia)=0.80
MS (FAB)=475
Empirical formula, MW: $C_{27}H_{46}N_4O_3$ (474.3)

PREPARATION EXAMPLE

General Formula I

EXAMPLE I

Nα-{Nδ-[1-(1-oxo)ethyl-[1-(5-S-amino-6-cyclohexyl-4-S-hydroxy-2-(1-methyl)ethylhexanoyl)]]-S-isoleucinyl}-2-pyridylmethylamide ter, dried and concentrated. On concentration a white solid crystallizes out.

Yield: 413 mg (80% of theory)
TLC: $R_f$(Ib)=0.69
MS (FAB)=517
Empirical formula, MW: $C_{29}H_{48}N_4O_4$ (516.73)

EXAMPLE II

Nα-{Nδ-[1-(1-butanoyl)-[1-(5-S-amino-6-cyclohexyl-4-S-hydroxy-2-(1-methyl)ethylhexanoyl)]]-S-isoleucinyl}-2-pyridylmethylamide

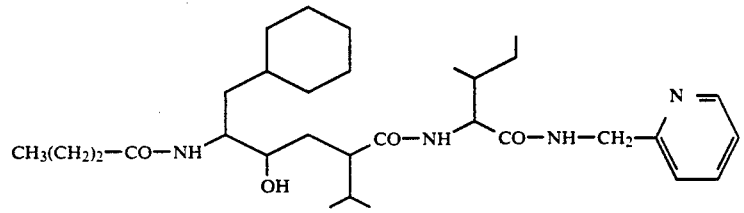

EXAMPLE III

Nα-{Nδ-[1-(3-methyl)butanoyl-[1-(5-S-amino-6-cyclohexyl-4-S-hydroxy-2-(1-methyl)ethylhexanoyl)]]-S-isoleucinyl}-2-pyridylmethylamide

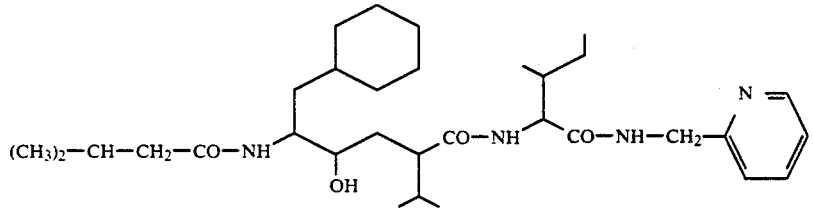

EXAMPLE IV

Nα-{Nδ-[1-(benzoyl)-[1-(5-S-amino-6-cyclohexyl-4-S-hydroxy-2-(1-methyl)ethylhexanoyl)]]-S-isoleucinyl}-2-pyridylmethylamide

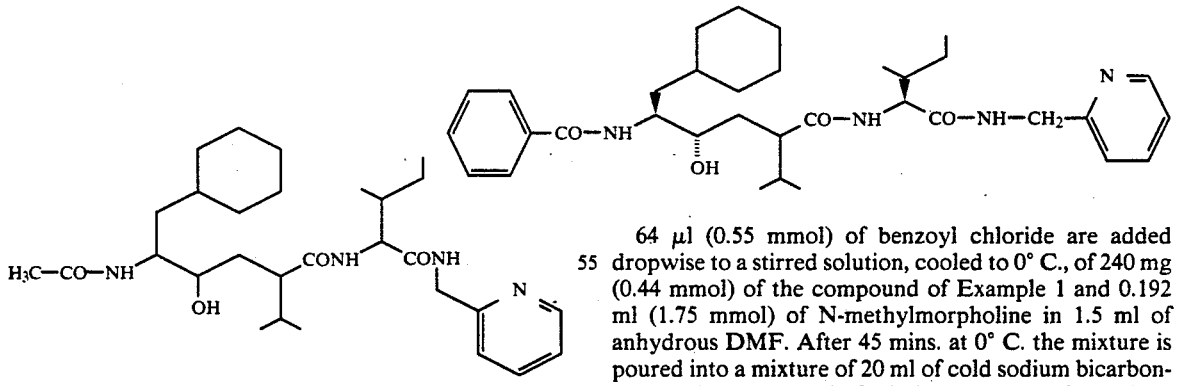

474 mg (1 mmol) of the compound from Example I are dissolved in 4 ml of dimethylformamide, and 113 μl of acetic anhydride and 146 μl of N-methylpiperidine are added. The solution is stirred for 4 h and concentrated. The residue is dispersed in ethyl acetate and saturated sodium bicarbonate solution. The organic phase is washed with potassium hydrogen sulphate solution (0.5M), is twice washed until neutral with wa- 64 μl (0.55 mmol) of benzoyl chloride are added dropwise to a stirred solution, cooled to 0° C., of 240 mg (0.44 mmol) of the compound of Example 1 and 0.192 ml (1.75 mmol) of N-methylmorpholine in 1.5 ml of anhydrous DMF. After 45 mins. at 0° C. the mixture is poured into a mixture of 20 ml of cold sodium bicarbonate solution and 10 ml of ethyl acetate and stirred thoroughly. The organic phase is separated off, the aqueous phase is extracted with 10 ml of ethyl acetate and the combined extracts are dried over magnesium sulphate. After evaporating off the solvent in vacuo and subjecting the raw product to chromatography on 20 g of silica gel (ethyl acetate), 32 mg (13%) of the non-polar isomer:

Rf=0.28 (ethyl acetate),

MS (FAB) m/e=579 (M+H)+, 601 (M+Na)+,
SF (MG): $C_{34}H_{50}N_4O_{4(578.81)}$,
and 62 mg (24%) of the polar isomer:
Rf=0.19 (ethyl acetate),
MS (FAB) m/e=579 (M+H)+, 601 (M+Na)+,
SF (MG): $C_{34}H_{50}N_4O_4$ (578.81),
are obtained.

Following the same procedure as in Example IV, 52 mg (46%) of the title compound were obtained in the form of a colourless powder from 100 mg (0.18 mmol) of the compound from Example 1 and 35 µl (0.23 mmol) of 1-naphthoyl chloride after chromatography of the raw product on 15 g of silica gel (ethyl acetate).

TLC: Rf=0.15 (ethyl acetate).
MS (FAB) m/e=629 (M+H)+,
SF (MG): $C_{38}H_{52}N_4O_4$ (628.87).

EXAMPLE V

Nα-{Nδ-[1-(4-methyl)benzoyl-[1-(5-S-amino-6-cyclohexyl-4-S-hydroxy-2-(1-methyl)ethylhexanoyl)]]-S-isoleucinyl}-2-pyridylmethylamide

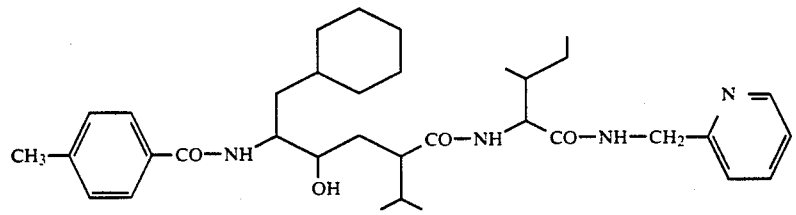

EXAMPLE VI

Nα-{Nδ-[1-(1-Naphthoyl)-[1-(5-S-amino-6-cyclohexyl-4-S-hydroxy-2-(1-methyl)ethylhexanoyl)]]-S-isoleucinyl}2-pyridylmethylamid

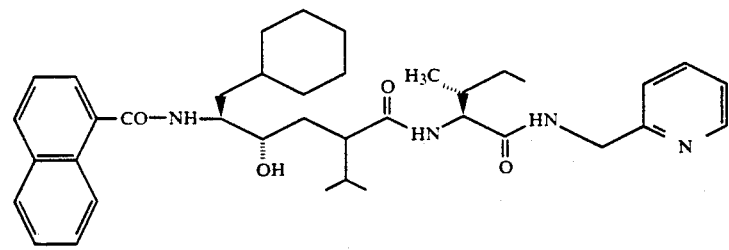

It is understood that the specification and examples are illustrative but not limitative of the present invention and that other embodiments within the spirit and scope of the invention will suggest themselves to those skilled in the art.

We claim:
1. A peptide of the formula

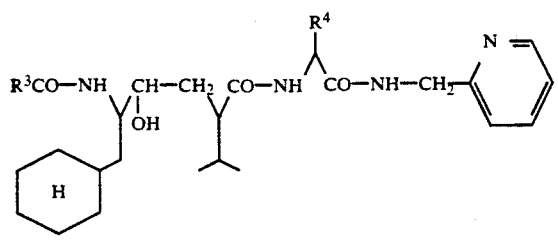

in which
$R^3$ denotes straight-chain or branched alkyl having up to 8 carbon atoms or
denotes aryl having 6 to 10 carbon atoms, and
$R^4$ denotes straight-chain or branched alkyl having up to 8 carbon atoms,
or a physiologically acceptable salt thereof.

2. A compound or salt thereof according to claim 1, in which
$R^3$ denotes straight-chain or branched alkyl having up to 6 carbon atoms, or phenyl, and
$R^4$ denotes straight-chain or branched alkyl having up to 6 carbon atoms.

3. A compound or salt thereof according to claim 1, in which
$R^3$ denotes straight-chain or branched alkyl having up to 4 carbon atoms, or phenyl, and
$R^4$ denotes straight-chain or branched alkyl having up to 4 carbon atoms.

4. A compound or salt according to claim 1, in which the radical

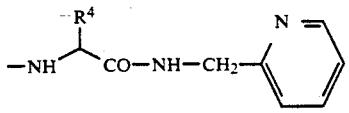

is in the L-form.

5. A compound or salt according to claim 1, in which the carbon atoms in the 1, 3 and 4 locations in the formula

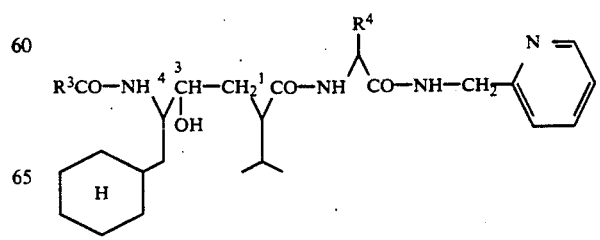

are present in the 1R, 3S, 4S-configuration, 1R, 3R, 4S-configuration, 1S, 3R, 4S-configuration or in the 1S, 3S, 4S-configuration.

6. A compound according to claim 1, wherein such compound is Nα-{Nδ-[1-(1-oxo)ethyl-[1-(5-S-amino-6-cyclohexyl-4-S-hydroxy-2-(1-methyl)ethylhexanoyl)]]-S-isoleucinyl}-2-pyridylmethylamide of the formula or a physiologically acceptable salt thereof.

7. A compound according to claim 1, wherein such compound is Nα-{Nδ-[1-(1-butanoyl)-[1-(5-S-amino-6-cyclohexyl-4-S-hydroxy-2-(1-methyl)ethylhexanoyl)]]-S-isoleucinyl}-2-pyridylmethylamide of the formula

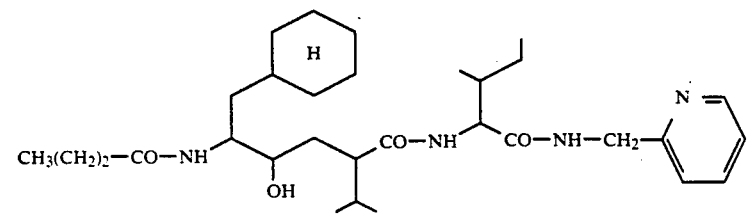

or a physiologically acceptable salt thereof.

8. A compound according to claim 1, wherein such compound is Nα-{Nδ-[1-(3-methyl)butanoyl-[1-(5-S-amino-6-cyclohexyl-4-S-hydroxy-2-(1-methyl)ethylhexanoyl)]]-S-isoleucinyl}-2-pyridylmethylamide of the formula

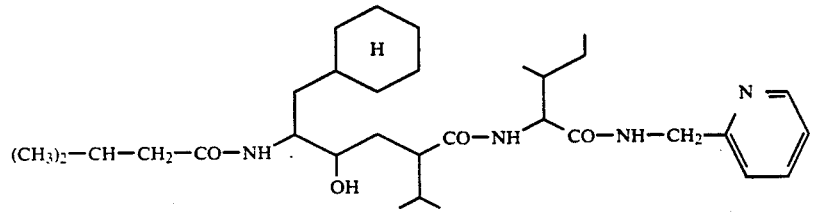

or a physiologically acceptable salt thereof.

9. A compound according to claim 1, wherein such compound is Nα-{Nδ-[1-(benzoyl)-[1-(5-S-amino-6-cyclohexyl-4-S-hydroxy-2-(1-methyl)ethylhexanoyl)]]-S-isoleucinyl}-2-pyridylmethylamide of the formula

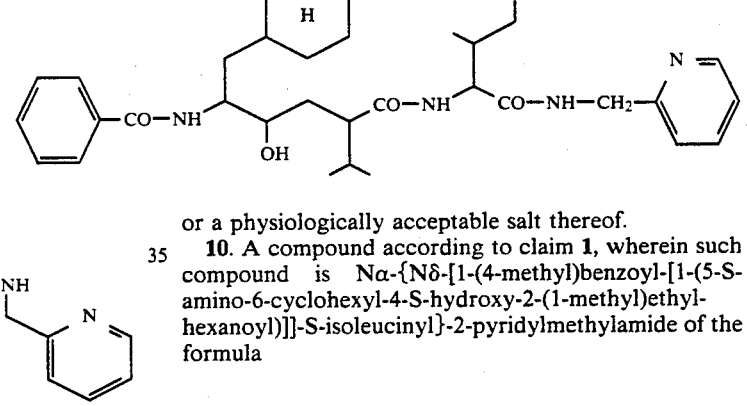

or a physiologically acceptable salt thereof.

10. A compound according to claim 1, wherein such compound is Nα-{Nδ-[1-(4-methyl)benzoyl-[1-(5-S-amino-6-cyclohexyl-4-S-hydroxy-2-(1-methyl)ethylhexanoyl)]]-S-isoleucinyl}-2-pyridylmethylamide of the formula

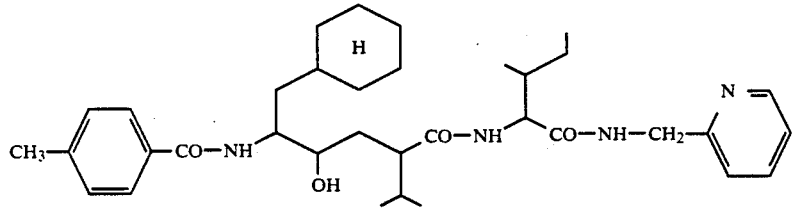

or a physiologically acceptable salt thereof.

11. A peptide of the formula

13
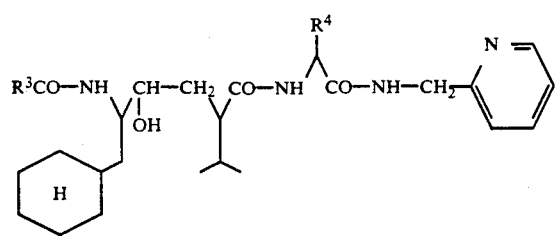
in which
R³ represents tolyl; and
R⁴ represents straight-chain or branched alkyl having up to 8 carbon atoms;
or a physiologically acceptable salt thereof.
* * * * *
14
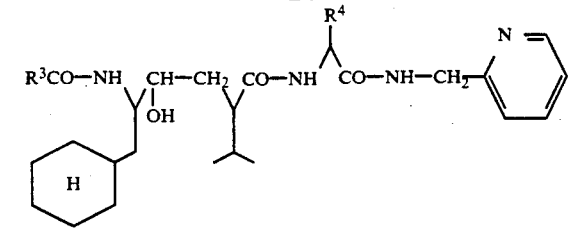
in which
R³ represents tolyl; and
R⁴ represents straight-chain or branched alkyl having up to 8 carbon atoms;
or a physiologically acceptable salt thereof.
* * * * *